United States Patent
Chen et al.

(10) Patent No.: US 11,890,128 B2
(45) Date of Patent: Feb. 6, 2024

(54) AUTOMATIC POSITIONING SYSTEM OF COMPUTED TOMOGRAPHY EQUIPMENT AND THE USING METHOD THEREOF

(71) Applicant: National Yang Ming Chiao Tung University, Taipei (TW)

(72) Inventors: Jyh-Cheng Chen, Taipei (TW); Chien-Heng Liu, Taipei (TW); Shih-Chun Jin, Taipei (TW)

(73) Assignee: NATIONAL YANG MING CHIAO TUNG UNIVERSITY, Taipei (TW)

( * ) Notice: Subject to any disclaimer, the term of this patent is extended or adjusted under 35 U.S.C. 154(b) by 139 days.

(21) Appl. No.: 17/473,031

(22) Filed: Sep. 13, 2021

(65) Prior Publication Data
US 2022/0240885 A1 Aug. 4, 2022

(30) Foreign Application Priority Data
Feb. 1, 2021 (TW) .................. 110103719

(51) Int. Cl.
*A61B 6/00* (2006.01)
*G01T 7/00* (2006.01)
*A61B 6/03* (2006.01)
*A61B 90/00* (2016.01)

(52) U.S. Cl.
CPC .............. *A61B 6/545* (2013.01); *A61B 6/032* (2013.01); *A61B 6/547* (2013.01); *A61B 6/582* (2013.01); *G01T 7/005* (2013.01); *A61B 2090/3966* (2016.02)

(58) Field of Classification Search
None
See application file for complete search history.

(56) References Cited

U.S. PATENT DOCUMENTS

| 7,031,427 | B2 * | 4/2006 | Dinten | .................... G06T 5/003 378/7 |
| 10,835,765 | B2 * | 11/2020 | Tulik | .................... A61N 5/1039 |
| 2019/0307415 | A1 * | 10/2019 | Antikainen | .......... A61B 6/4007 |

* cited by examiner

*Primary Examiner* — Dani Fox
(74) *Attorney, Agent, or Firm* — Muncy, Geissler, Olds & Lowe, P.C.

(57) ABSTRACT

The present invention provides an automatic positioning system of computed tomography equipment and a method for automatically positioning computed tomography equipment. By the system and the method of the present invention, a geometric locating correction is able to be made on the equipment before operating it. After the correction, the focal spot of the X-ray tube of the computed tomography equipment and the center of the X-ray detector are on the same straight line, so that a projection image close to the real image can be obtained to avoid offset or distortion in subsequent 3D mapping.

4 Claims, 4 Drawing Sheets

AUTOMATIC POSITIONING SYSTEM OF COMPUTED TOMOGRAPHY EQUIPMENT AND THE USING METHOD THEREOF

CROSS-REFERENCE TO RELATED APPLICATION

This application claims priority of Taiwanese Application No. 110103719, filed on Feb. 1, 2021.

BACKGROUND OF THE INVENTION

Technical Field of the Invention

The present invention relates to an automatic positioning system for computed tomography (CT) equipment and an automatic positioning method of the system, wherein the system comprises a detector fixing jig, an X-Y linear moving rail for horizontal and vertical movement, and an X-ray detector. Particularly, the automatic positioning method performs an alignment correction to the CT equipment before the CT scan is performed.

Background

Computed tomography (CT) is a three-dimensional (3D) radiographic medical image generated by using rotating X-ray to irradiate human body and a digital geometric processor of computer to reconstruct the 3D radiographic image of patient. In medical field, doctors can diagnose patients through 3D body image obtained by CT for optimizing the treatment plan before surgery or achieving a better result of diagnosing lesions; in dentistry, CT also plays a very important role in helping dentists to diagnose the teeth condition of patient.

Image reconstruction, which has always been an important subject of CT-related research, is reconstructing a 3D image of a space by calculating images collected from different angles. During reconstruction, the geometric structure of CT equipment will strongly affect the quality of the reconstructed image. Ideally, the focal spot of the equipment's X-ray tube and the center of the detector will be collinear, and the whole equipment will rotate the irradiated object's center of rotation which is also collinear; however, in the practice, the positioning error of the equipment caused by artificial measurement error and gravity issue is increased over time. Therefore, before performing CT imaging or reconstruction, a geometric correction is required for obtaining a projection image close to the real situation.

Geometric correction is conducted by finding geometric deviations and geometric parameters thereof through images, substituting them into re-mapping step, correcting the original projection with deviations, and then staring the image reconstruction. It is obvious that geometric correction is a very important part in the 3D image reconstruction related studies. However, with the current technology, there still some errors caused by artificial or mechanical actions will make the corrected plane deviate. These uncertain factors greatly affect the using condition of current CT equipment.

Generally speaking, there are two types of calibration methods for CT equipment, one is using a phantom, and the other is conducting a synchronous geometric correction. For example, cone beam compute tomography (CBCT), which is widely used in many fields, can be applied to obtain cross-sectional images of object. There are two methods for geometric correction of CBCT. The first one is using a projection of a specific phantom for analytically calculating geometric parameters. The disadvantage of this method is that the geometric parameters need to be calculated before the experiment, but there might be some geometric changes of the equipment between two scans. The other one is synchronous geometric correction, which allows user to only perform one irradiation on the object to calculate the geometric parameters, but this method also has some disadvantages and fails to calculate the complete geometric parameters.

The current CT equipment all need to use a specific phantom to confirm whether the plane on which the measured object positions deviates from the scanning center. If there is a deviation, it might cause offset or distortion in subsequent 3D image reconstruction. Even though the correction is completed, or the equipment is used for a long time, the corrected plane still may be deviated due to artificial or mechanical actions. The above uncertain factors greatly affect the use of the CT equipment.

In prior art, many related manufactures have developed several alignment correction systems through a correction phantom. Most of them are based on the design that X-ray tube anode target, the rotation center, and the center of detector are collinear for conducting alignment origin correction. However, this method is not easy to be very accurate.

Therefore, the present invention provides an automatic positioning system for CT equipment and an automatic positioning method for performing geometric correction in order to solve the above-mentioned problems. Particularly, the method is to conduct an alignment correction on the equipment before performing it and carry out an image reconstruction of object projections from various angles after the alignment correction to eliminate image defects.

SUMMARY OF INVENTION

Through the system and method provided by the present invention, the origin of CT equipment is calibrated quickly and accurately.

First of all, the present invention provides an automatic positioning system for positioning CT equipment, which comprises a detector fixing jig, a calibration bead, a flat plate with low X-ray attenuation, an X-Y linear moving rail for horizontal and vertical movement, an X-ray detector, a control module, a driving module and an image processing unit, wherein the X-ray detector is linked to the detector fixing jig which is fixed on the linear moving rail, wherein the linear moving rail is installed on the detector end of a CT equipment needs to be positioned and linked with the X-ray tube end of the CT equipment through the rotating arm of the CT equipment for allowing the X-ray detector to move horizontally and vertically.

In one embodiment, the detector fixing jig is a long, plate-shaped, and high weight capacity metal, and is linked with the linear moving rail.

In one embodiment, the calibration bead is a high-density metal sphere with a diameter of less than 1.0 mm, and the calibration bead is embedded in the flat plate with low X-ray attenuation and placed in front of the X-ray tube window.

In another embodiment, the image processing unit which is electrically connected to the control module can perform a positioning procedure on a reference image to calculate a space vector. After calculating a displacement vector from the reference image to the center of the X-ray detector, the displacement vector is sent to the control module for being converted into a calibration instruction which will be fed back to the control module, wherein the image processing unit is a computer that can process and calculate images.

In one embodiment, the driving module is electrically connected to the control module, and the driving module performs displacement and correction on the X-ray detector according to the calibration instruction, wherein the driving module is a motor, and the control module is a computer system with equipment driver.

The present invention also provides a method for automatically positioning CT equipment, which comprises the following steps:

S201: installing a calibration bead in front of the X-ray tube window of a computed tomography (CT) equipment;

S202: initiating the CT equipment to irradiate the calibration bead by X-ray to project a calibration image on an X-ray detector;

S203: obtaining a coordinate (X, Y) of the calibration image on the X-ray detector by an image processing unit;

S204: calculating a displacement vector (ΔU, ΔV) from the coordinate to the center of the X-ray detector;

S205: calculating the displacement vector (ΔU, ΔV) by an image processing unit to generate a calibration instruction for driving a driving module to adjust the position of the X-ray detector, so that the center of the X-ray detector (Uc, Vc) overlaps with the coordinate (X, Y) of the calibration image as a preliminary correction;

S206: confirming that the calibration image is exactly overlapping with the center of the X-ray detector for completing positioning; if they are not overlapped, returning to step S204 to capture another calibration image of the calibration bead again; and S207: the calibration is completed.

DETAILED DESCRIPTION OF THE INVENTION

Unless otherwise defined herein, the technical terms and scientific terms used in this specification are definitions commonly known to a person having ordinary skill in the art.

The present invention can be further elucidated by the following examples. These exemplary embodiments are only used for description instead of limiting the application and the scope of the present invention.

Example 1. Automatic Positioning System of CT Equipment

Figure 1:
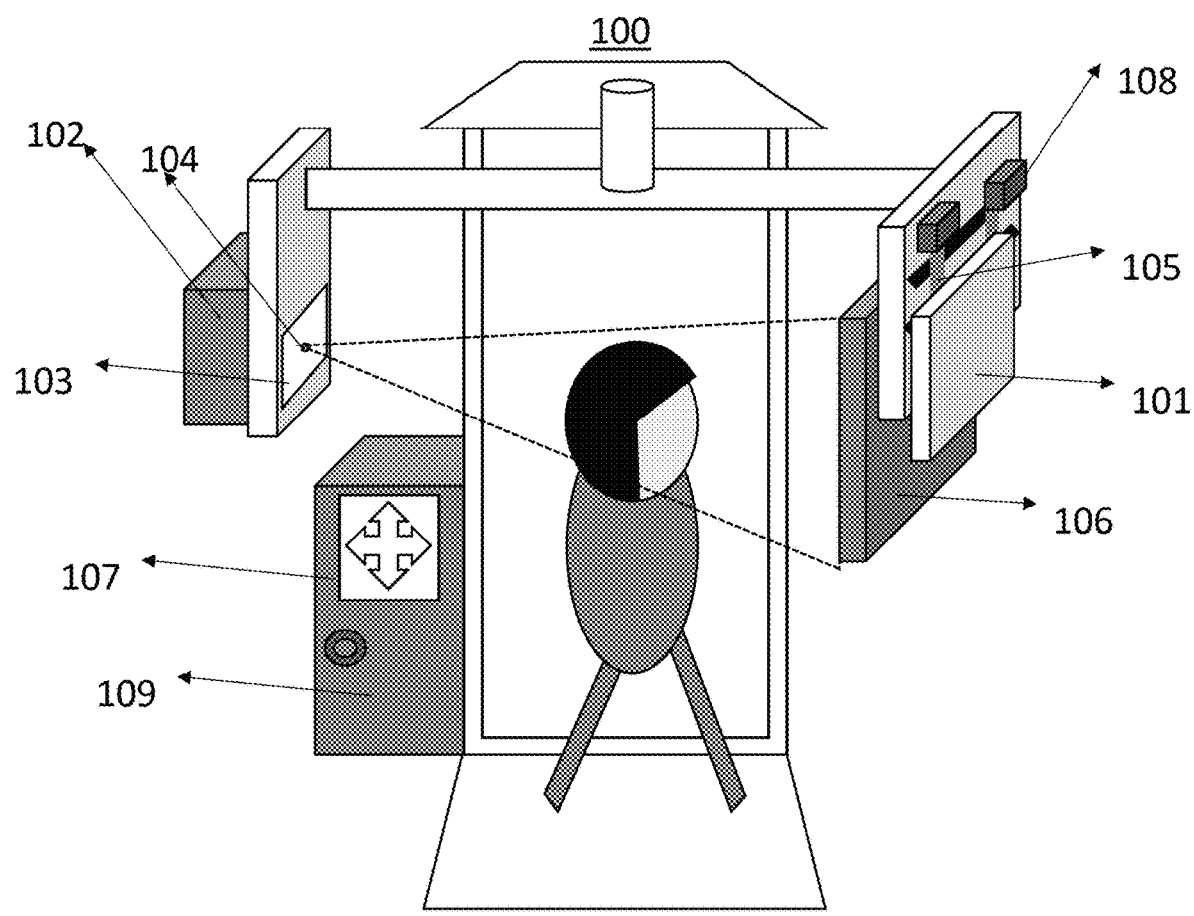
FIG. 1 is a structural diagram of the automatic positioning system of CT equipment provided by the present invention.

Please refer to FIG. 1, the present invention provides a positioning system 100 for automatically positioning CT equipment comprising a detector fixing jig 101, an X-ray generator 102, a flat plate with low X-ray attenuation 103, a calibration steal bead 104, an X-Y linear moving rail (or slide rail) 105 for horizontal and vertical movement, an X-ray detector 106, a control module 107, a driving module 108 and an image processing unit 109, wherein the detector fixing jig 101 is installed on the X-Y linear moving rail 105 and the X-ray detector 106 is linked with the detector fixing jig 101, wherein the linear moving rail 105 is installed on the detector end of a CT equipment needed to be positioned and linked with the X-ray tube end of the CT equipment through the rotating arm of the CT equipment for allowing the X-ray detector 106 to move horizontally and vertically.

The calibration steel bead 104 is a steel bead with a diameter of less than 1.0 mm and embedded in the flat plate with low X-ray attenuation 103 and placed in front of the X-ray tube window of the X-ray generator 102.

In the positioning system provided by the present invention, the image processing unit 109 is a computer that can process and calculate images and is electrically connected to the control module 107 for performing a positioning procedure of images and calculating space vectors. After calculating a displacement vector from the projected image to the center of the X-ray detector 106, the displacement vector is sent to the control module 107 for being converted into a calibration instruction which will be fed back to the control module 107; and the driving module 108 is a motor and is electrically connected to the control module 107, and the driving module 108 performs displacement and correction on the X-ray detector 106 according to the calibration instruction.

Figure 2:
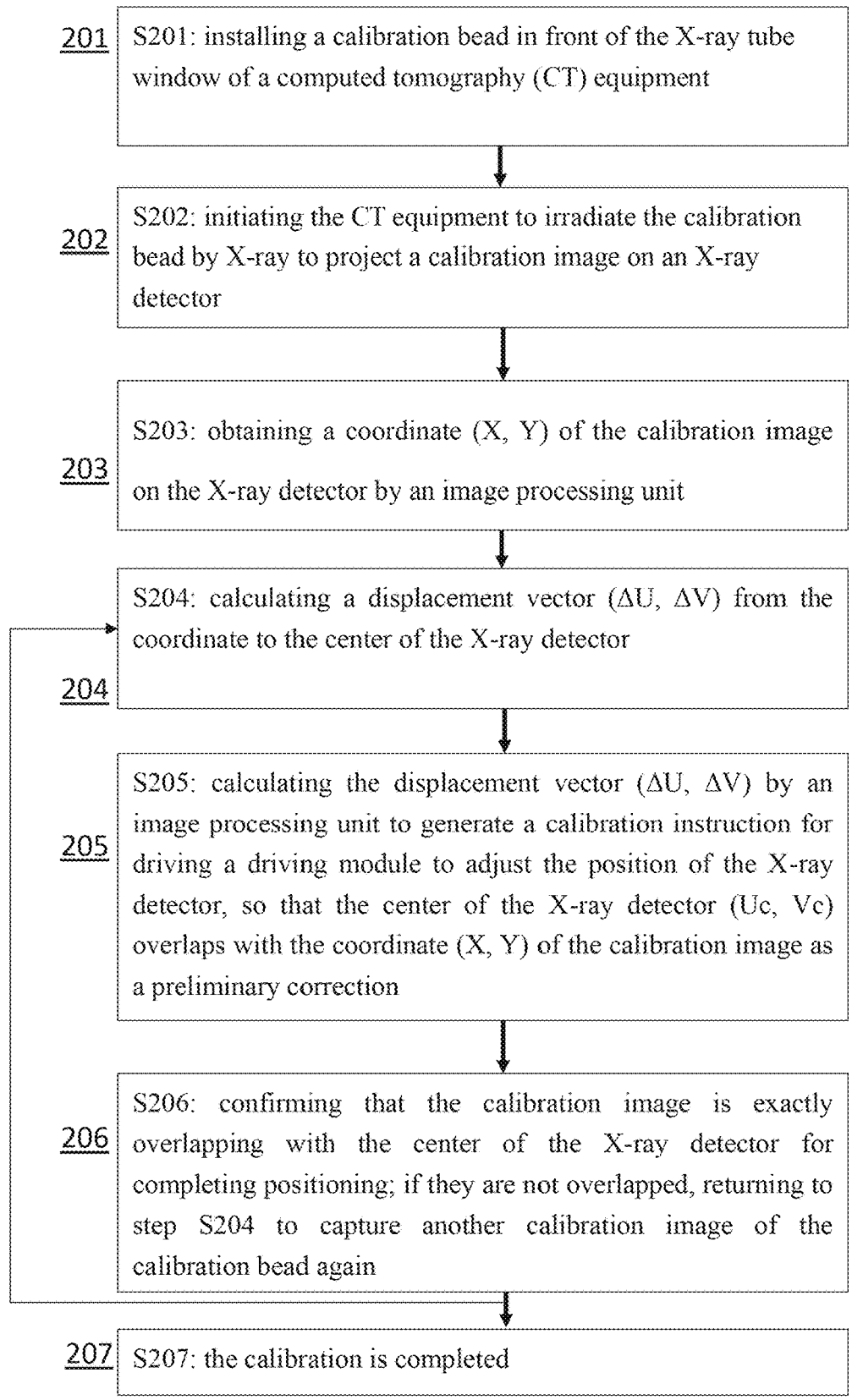
FIG. 2 is a flow chart showing the method of the present invention for automatically positioning a CT equipment.

Example 2. The Method for Automatically Positioning a Computed Tomography (CT) Equipment Please refer to FIG. 2, the present invention provides a method for automatically positioning a CT equipment, which comprises the following steps:

S201: installing a calibration bead in front of the X-ray tube window of a computed tomography (CT) equipment;

S202: initiating the CT equipment to irradiate the calibration bead by X-ray to project a calibration image on an X-ray detector;

S203: obtaining a coordinate (X, Y) of the calibration image on the X-ray detector by an image processing unit;

S204: calculating a displacement vector (ΔU, ΔV) from the coordinate to the center of the X-ray detector;

S205: calculating the displacement vector (ΔU, ΔV) by an image processing unit to generate a calibration instruction for driving a driving module to adjust the position of the X-ray detector, so that the center of the X-ray detector (Uc, Vc) overlaps with the coordinate (X, Y) of the calibration image as a preliminary correction;

S206: confirming that the calibration image is exactly overlapping with the center of the X-ray detector for completing positioning; if they are not overlapped, returning to step S204 to capture another calibration image of the calibration bead again; and S207: the calibration is completed.

Briefly, first of all, installing the calibration bead in front of the X-ray tube window of the CT equipment and initiating the CT equipment to irradiate the calibration bead to project a calibration image on the X-ray detector. In the meanwhile, the image processing unit and the control module are determining and calculating the position and the vector of the calibration image by determining the coordinate position of the calibration image on the X-ray detector based on the boundary information of the calibration image and detecting the coordinate position of the projected image of the calibration bead's centroid point in the calibration image to calculate the displacement between the calibration bead and the center of the X-ray detector and converse the coordinate. At this point, the offset of the calibration bead projection's centroid point is detected, which means that the current focal spot of the X-ray tube and the center of the detector are not on the same straight line. Therefore, the control module is used to conduct the required displacement for X-Y axis and sends the calibration instruction of displacement correction to the driving module. Based on the calibration instruction, the driving module will perform a displacement of the X-ray detector in X-Y axis, so that the calibration bead projection's centroid point is overlapping with the center of the X-ray detector, which means that the focal spot of the X-ray tube and the center of the detector fall on the same straight line. The above is a completion of the first preliminary calibration. If the calibration is still not successful after the preliminary calibration or another calibration or confirmation of the calibration result is required for any other reason, the above steps can be repeated.

Figure 3:
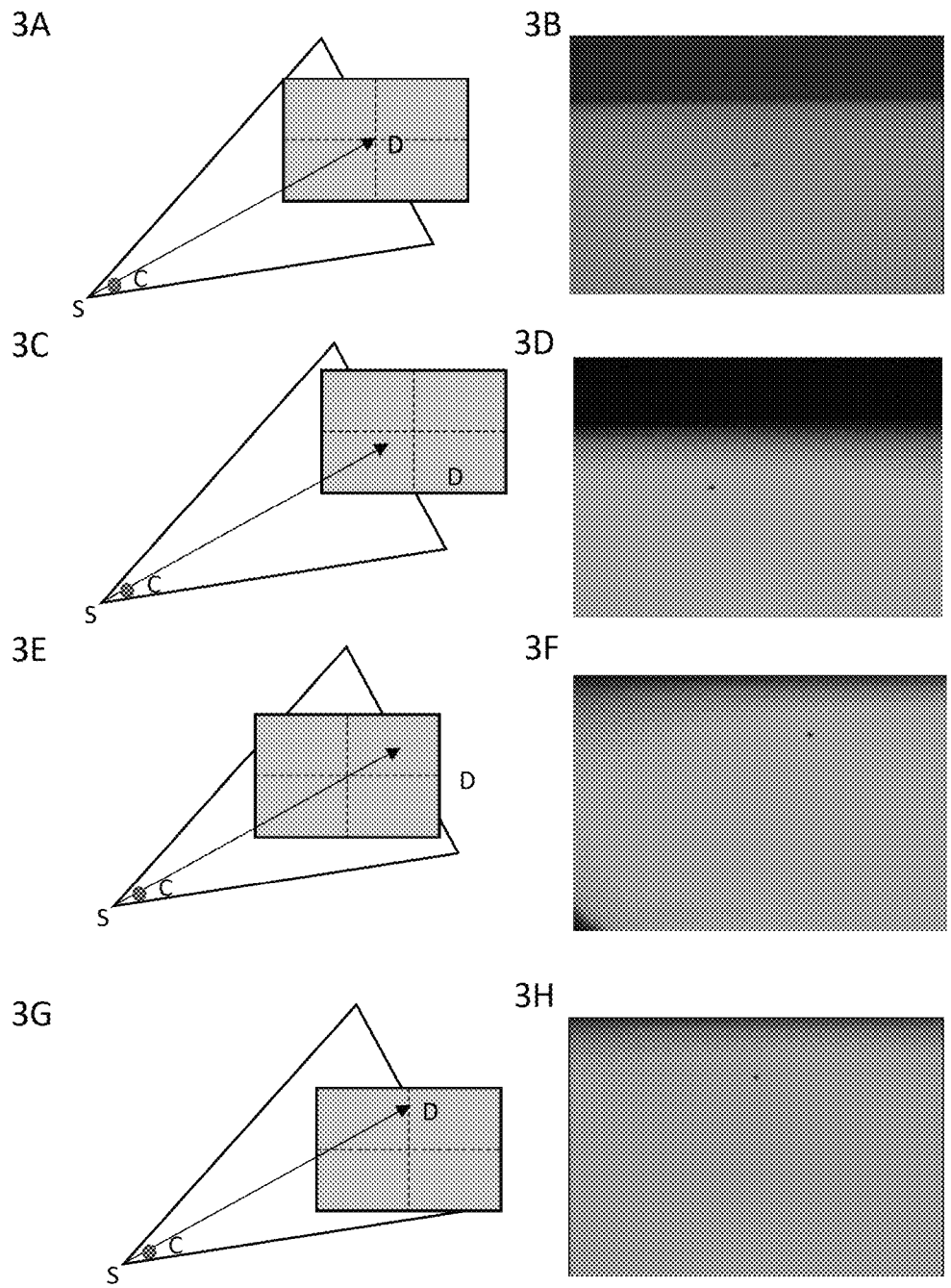
FIG. 3 is a schematic diagram showing the relative positions of a CT equipment before and after conducting the automatic positioning method of present invention.

Please refer to FIG. 3, a schematic diagram showing the X-ray projection image of the CT equipment before and after the calibration and the relationship between these images and the position of the system. As shown in FIG. 3A, wherein S is the X-ray center and lined up with C, the position of the calibration bead. Ideally, S, C and D, the center of the X-ray detector, should be collinear, which is the purpose of the present invention, and the corresponding image is shown in FIG. 3B. Before, the calibration of the equipment, the relative position relationship diagram are as follows: the projection of the calibration bead is at the lower left limit point as shown in FIG. 3C, and the corresponding resulting image is shown in FIG. 3D; the projection of the calibration bead is at the upper right limit point as shown in FIG. 3E, and the corresponding resulting image is shown in FIG. 3F; and the projection of the calibration bead is on the central line but not at the center is shown in FIG. 3G, and the corresponding resulting image is shown in FIG. 3H. The above projecting situations can be corrected by the calibration method of present invention and returned to the ideal situation.

Example 3. Confirming the Correctness of the Present Method by Using a Phantom

In this embodiment, two of the most commonly used calibration methods in the prior art are used as control groups, which respectively are 3 mm capillary phantom 401 image (FIG. 4A-4C) or an acrylic cylindrical phantom (FIG. 4D-4F), for comparing the positioning and calibrating methods.

Figure 4:
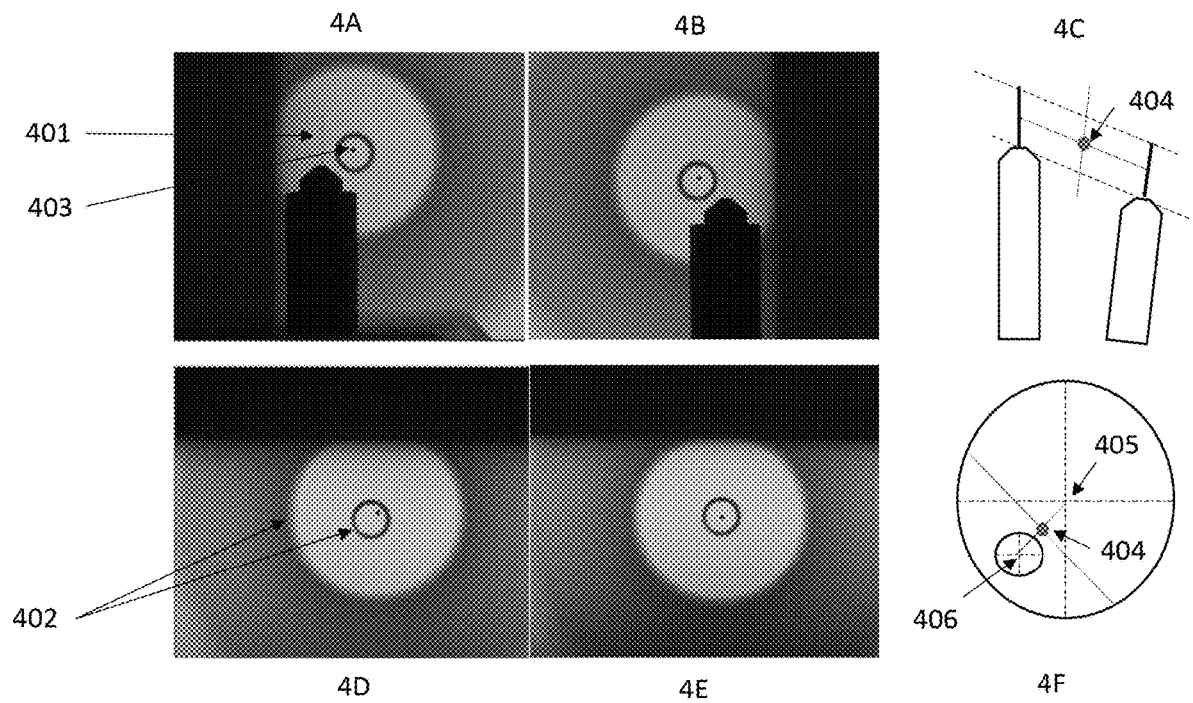
FIG. 4 is a flow chart showing the embodiment of the method for automatically positioning a CT equipment provided by the present invention.

In the positioning and calibrating method of capillary phantom, the theory of it is collecting the projecting images of the capillary phantom at the two opposite sides of the X-ray detector's center as shown in FIGS. 4A and 4B. By finding the end point positions of the capillary phantom in two images and obtaining a total of four positions, the center point of these positions is the calibration midpoint 404 of the system (as shown in FIG. 4C).

On the other hand, the method of using acrylic cylindrical phantom is the standard procedure for calibrating X-ray equipment in general hospitals. Briefly, the projections of two circular holes in the front and back of the acrylic phantom in different magnifications will form two concentric circles 402. The image without calibration is shown in FIG. 4D and the calibrated image is shown in FIG. 4E. The calibration is conducting by observing if the centers (405 and 406) of two concentric circles is overlapping, and the calibration is completed when the centers (405 and 406) are adjusted to completely coincide with the calibration midpoint 404 of the system. However, the disadvantage of this method is that the whole process requires visual observations which is hard to be intuitional.

The method provided by the present invention is a direct and effective calibration method that determining if the calibration bead's projection 403 is at the center of the image is used as calibration means. And through the verification with the aforementioned two calibration methods, it is proved that the method of using a calibration bead projection can effectively improve the shortcomings of prior arts.

The invention claimed is:
1. An automatic positioning system for positioning computed tomography (CT) equipment, which comprises
 a detector fixing jig; a calibration bead; a flat plate with low X-ray attenuation;
  an X-Y linear moving rail for horizontal and vertical movement; an X-ray detector; a control module; a driving module; an image processing unit;
  wherein the X-ray detector is linked to the detector fixing jig which is fixed on the linear moving rail;
  wherein the linear moving rail is installed on a detector end of a CT equipment needed to be positioned and linked with an X-ray tube end of the CT equipment through a rotating arm of CT equipment for allowing the X-ray detector to move horizontally and vertically;
  wherein the calibration bead is embedded in the flat plate with low X-ray attenuation and is placed in front of the window of the X-ray tube;
  wherein the image processing unit is electrically connected to the control module and the driving module is electrically connected to the control module; and
  wherein the image processing unit processes an image positioning procedure to calculate space vectors and calculating a displacement vector from the projected image to the center of the X-ray detector, wherein the displacement vector is sent to the control module for being converted into a calibration instruction which is fed back to the control module and the driving module performs displacement and correction on the X-ray detector according to the calibration instruction.
2. The automatic positioning system according to claim 1, wherein the calibration bead is a sphere with a diameter of less than 1.0 mm and is made of high-density metal comprising steel, cooper, nickel, and chromium.
3. A method for automatically positioning CT equipment, which comprises: installing a calibration bead in front of the window of X-ray tube of a CT equipment; initiating the CT equipment to irradiate the calibration bead by X-ray to project a first calibration image on an X-ray detector; obtaining a coordinate of the first calibration image on the X-ray detector by an image processing unit and calculating a displacement vector from the coordinate to the center of the X-ray detector; calculating the displacement vector by an image processing unit to generate a calibration instruction for driving a control module to adjust the position of the X-ray detector, so that the center of the X-ray detector overlaps with the first calibration image; obtaining a second calibration image of the calibration bead; and confirming that the second calibration image is exactly overlapping with the center of the X-ray detector for completing positioning.

4. The method according to claim 3, wherein if the second calibration image of the calibration bead is not overlapping with the center of the X-ray detector, a displacement vector from a coordinate of the second calibration image of the calibration bead on the X-ray detector to the center of the X-ray detector.

* * * * *